(12) United States Patent
Zino (10) Patent No.: US 8,532,738 B2
(45) Date of Patent: Sep. 10, 2013

(54) VISUALIZATION OF CATHETER-TISSUE CONTACT BY MAP DISTORTION

(75) Inventor: Eliahu Zino, Atlit (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 105 days.

(21) Appl. No.: 12/939,259

(22) Filed: Nov. 4, 2010

(65) Prior Publication Data

US 2012/0116210 A1 May 10, 2012

(51) Int. Cl.
*A61B 5/05* (2006.01)

(52) U.S. Cl.
USPC ........... 600/407; 600/410; 600/411; 600/421; 600/424; 600/425; 600/427; 600/431; 600/433; 600/434; 600/435; 600/437; 600/466; 600/467

(58) Field of Classification Search
USPC ................. 600/407, 410, 411, 421, 424, 425, 600/427, 431, 433, 434, 435, 437, 466, 467
See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |
| 5,558,091 A | 9/1996 | Acker et al. | |
| 5,944,022 A | 8/1999 | Nardella et al. | |
| 5,983,126 A | 11/1999 | Wittkampf | |
| 6,172,499 B1 | 1/2001 | Ashe | |
| 6,177,792 B1 | 1/2001 | Govari et al. | |
| 6,216,027 B1 * | 4/2001 | Willis et al. | 600/424 |
| 6,298,257 B1 * | 10/2001 | Hall et al. | 600/407 |
| 6,456,864 B1 | 9/2002 | Swanson et al. | |
| 6,690,963 B2 | 2/2004 | Ben-Haim et al. | |
| 6,788,967 B2 | 9/2004 | Ben-Haim et al. | |
| 6,892,091 B1 * | 5/2005 | Ben-Haim et al. | 600/509 |
| 8,311,791 B1 * | 11/2012 | Avisar | 703/11 |
| 2002/0120188 A1 | 8/2002 | Brock et al. | |
| 2006/0278248 A1 | 12/2006 | Viswanathan | |
| 2007/0100332 A1 | 5/2007 | Paul et al. | |
| 2008/0009750 A1 | 1/2008 | Aeby | |
| 2009/0076476 A1 | 3/2009 | Barbagli et al. | |
| 2009/0093806 A1 | 4/2009 | Govari et al. | |
| 2009/0138007 A1 | 5/2009 | Govari et al. | |

(Continued)

FOREIGN PATENT DOCUMENTS

| | | |
|---|---|---|
| EP | 2 201 890 A1 | 6/2010 |
| EP | 2 248 480 A1 | 11/2010 |
| WO | WO 2007/015139 A2 | 2/2007 |

(Continued)

OTHER PUBLICATIONS

Extended European Search Report dated Mar. 14, 2012 from related EP Application No. 11187708.0.

*Primary Examiner* — James Kish (74) *Attorney, Agent, or Firm* — Louis J. Capezzuto (57) ABSTRACT

A method, including constructing a simulated surface of a body cavity, and pressing a distal end of a probe against a wall of the body cavity. While pressing the distal end against the wall, position measurements are accepted from the probe indicating a position of the probe within the body cavity, and force measurements are accepted from the probe indicating a force between the distal end and the wall. A distortion in the simulated surface is created at the position indicated by the position measurements, so as to form a distorted surface, upon detecting that the force measurements exceed a predefined amount. The distorted surface is then displayed.

17 Claims, 4 Drawing Sheets

(56) References Cited

U.S. PATENT DOCUMENTS

| | | | |
|---|---|---|---|
| 2009/0226069 A1* | 9/2009 | Razzaque et al. | 382/131 |
| 2009/0262109 A1 | 10/2009 | Markowitz et al. | |
| 2010/0069921 A1 | 3/2010 | Miller et al. | |
| 2010/0169815 A1 | 7/2010 | Zhao et al. | |

FOREIGN PATENT DOCUMENTS

| | | |
|---|---|---|
| WO | WO 2007/098494 A1 | 8/2007 |
| WO | WO 2009/029627 A1 | 3/2009 |

\* cited by examiner

VISUALIZATION OF CATHETER-TISSUE CONTACT BY MAP DISTORTION

FIELD OF THE INVENTION

The present invention relates generally to medical imaging, and specifically to visualizing a force exerted by a medical probe on intra-body tissue.

BACKGROUND OF THE INVENTION

In electrophysiological diagnostic procedures such as intracardiac electrical mapping, an invasive medical probe is introduced into a cavity of a body organ. As the probe is positioned at specific points within the organ, the probe measures specific information (e.g., an electrical potential) and conveys the measurements to a mapping system. The mapping system creates a map comprising the measurements at their respective locations in the organ. The map can be used in applying various diagnostic and therapeutic procedures to the organ.

When placing the probe within the organ, it may be desirable to have the distal tip of the probe in direct contact with organ tissue. The contact can be verified, for example, by measuring the contact pressure between the distal tip and the tissue. U.S. Patent Application Publications 2007/0100332, 2009/0093806 and 2009/0138007, whose disclosures are incorporated herein by reference, describe methods of sensing contact pressure between the distal tip of a catheter and tissue in a body cavity using a force sensor embedded in the catheter.

SUMMARY OF THE INVENTION

There is provided, in accordance with an embodiment of the present invention, a method, including constructing a simulated surface of a body cavity, pressing a distal end of a probe against a wall of the body cavity, while pressing the distal end against the wall, accepting, from the probe, position measurements indicating a position of the probe within the body cavity and force measurements indicating a force between the distal end and the wall, creating a distortion in the simulated surface at the position indicated by the position measurements, so as to form a distorted surface, upon detecting that the force measurements exceed a predefined amount, and displaying the distorted surface.

The method may include, at a time prior to constructing the simulated surface, collecting, from a medical imaging system, image data for the body cavity. In some embodiments, the medical imaging system may be selected from a group consisting of a probe mapping system, a magnetic resonance imaging system and a computed tomography system. In another embodiment, constructing the simulated surface may include applying a fast mapping process to the image data. In an additional embodiment, the probe may include an intracardiac catheter. In yet another embodiment, the body cavity may include a chamber of a heart. In still yet another embodiment, creating the distortion may include incorporating a three dimensional effect on the simulated surface. In an alternative embodiment, the three dimensional effect may include a vertex protruding from the simulated surface. In a further embodiment, the three dimensional effect may include a vertex recessing into the simulated surface. In another embodiment, creating the distortion may include filling a region of the simulated surface with a specific color corresponding to the force at the position indicated by the position measurements.

There is also provided, in accordance with an embodiment of the present invention an apparatus including a probe and a processor. The probe is configured for insertion into a body cavity of a patient and includes a position sensor for measuring a position of a distal end of the probe inside the body cavity and a force sensor for measuring a force between the distal end and a wall of the body cavity. The processor is configured to construct a simulated surface of the body cavity, to accept from the probe, while pressing the distal end against the wall, position measurements indicating a position of the probe within the body cavity and force measurements indicating a force between the distal end and the wall, to create a distortion in the simulated surface at the position indicated by the position measurements, so as to form a distorted surface, upon detecting that the force measurements exceed a predefined amount, and to display the distorted surface.

There is further provided, in accordance with an embodiment of the present invention, a computer software product, operated in conjunction with a probe that is configured for insertion into a body cavity of a patient and includes a position sensor for measuring a position of a distal end of the probe inside the body cavity and a force sensor for measuring a force between the distal end and a wall of the body cavity, the product including a non-transitory computer-readable medium, in which program instructions are stored, which instructions, when read by a computer, cause the computer to construct a simulated surface of the body cavity, to accept from the probe, while pressing the distal end against the wall, position measurements indicating a position of the probe within the body cavity and force measurements indicating a force between the distal end and the wall, to create a distortion in the simulated surface at the position indicated by the position measurements, so as to form a distorted surface, upon detecting that the force measurements exceed a predefined amount, and to display the distorted surface.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Physiological or anatomical mapping procedures typically create a map comprising map points collected from an electroanatomical mapping system. Each map point comprises a respective coordinate within a body organ, and possibly a physiological property collected by a medical probe at the respective coordinate.

When collecting the map points, it is important to maintain the proper level of force between the probe and body cavity tissue, such as a heart wall. Sufficient force is needed in order to ensure good electrode contact between the probe and the tissue. Poor electrical contact can result in inaccurate readings. On the other hand, excessive force can deform the tissue and thus distort the map. In severe cases, too much force may cause physical damage to the heart wall.

Embodiments of the present invention provide methods and systems for visualizing a contact force between a force-sensing probe such as an intracardiac catheter, and intra-body tissue such as a heart wall. In some embodiments, a simulated surface is constructed for the heart wall based on data points received from a medical imaging system. When the force-sensing probe applies a force to the heart wall, a distortion may be created on the simulated surface at the point of contact. The distortion may be presented graphically as a protruding vertex on the simulated surface corresponding to the location of the catheter-tissue contact, thereby presenting a three dimensional (3D) view of the heart wall to an operator such as a medical professional.

When viewing the distortion from outside the heart chamber, the graphical effect of the distortion may be similar to the sort of protruding bump that is observed when a stick is pushed against an elastic cloth. Alternatively, the distortion may be visualized from the inside of the heart chamber as a vertex recessed in the simulated surface (i.e., a depression). In alternative embodiments, in a manner similar to hypsometric tinting and shaded relief methods that are used in cartography, the distortion may use coloring and/or shading to indicate the force between the catheter and the intra-body tissue, where different colors or shadings correspond to different force levels.

The amount of distortion shown in the simulated surface may not necessary reflect the actual distortion of the heart wall resulting from the force. Embodiments of the present invention allow the operator to adjust the amount of distortion for visualization purposes. Additionally or alternatively, different relative degrees of distortion may be used under different circumstances. For example, greater distortion may be presented in atria than in ventricles (atria typically have thinner walls that ventricles), when the catheter applies a similar force.

In some embodiments, the distortion indicating catheter-tissue contact may display not only the point of contact, but may also display the contact force, by increasing the distortion of the simulated surface in proportion to the force between the catheter and the intra-body tissue.

System Description

Figure 1:
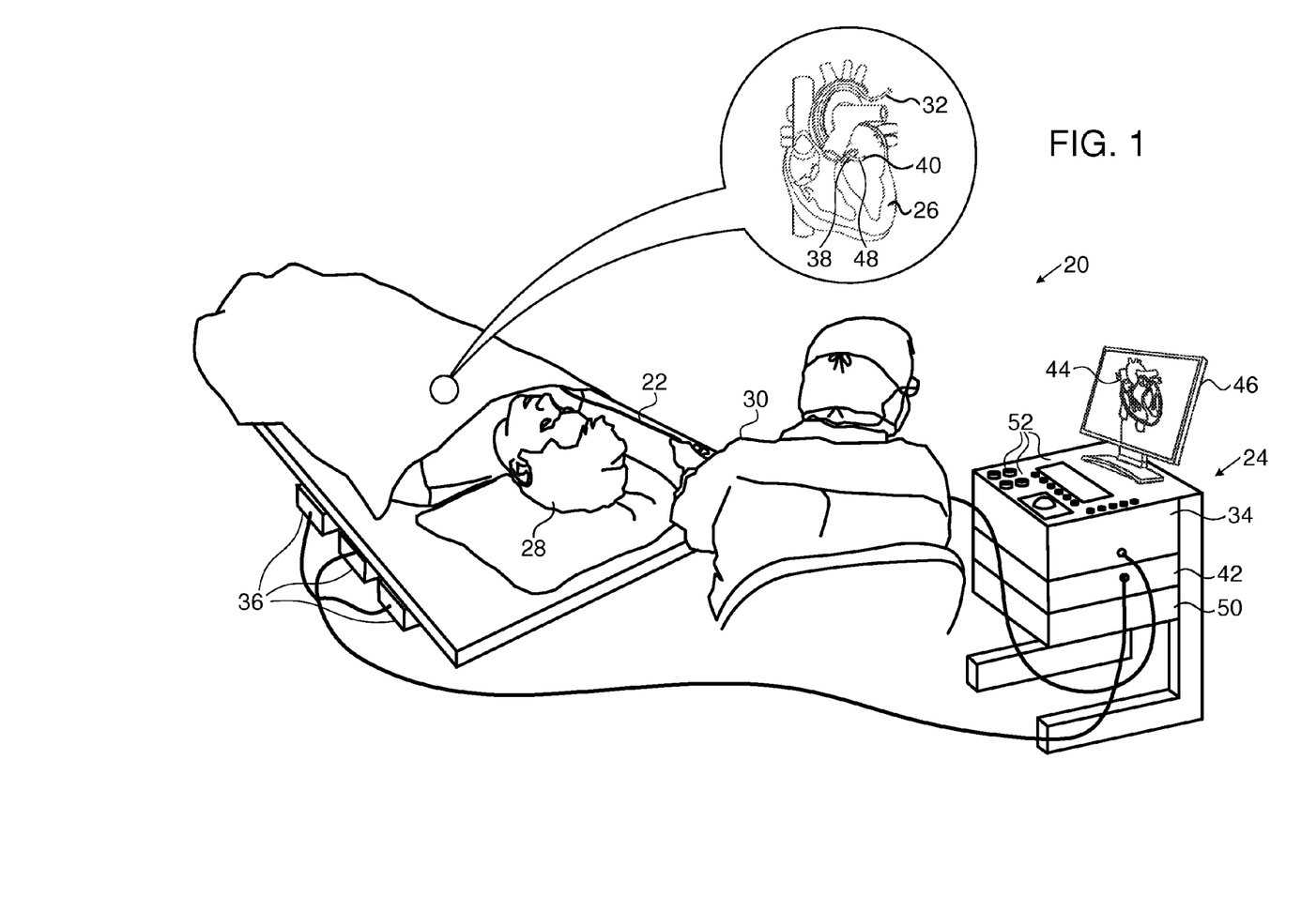
FIG. 1 is a schematic pictorial illustration of a catheter-tissue contact visualization system for a force-sensing catheter, in accordance with an embodiment of the present invention.

FIG. 1 is a schematic, pictorial illustration of an intracardiac mapping system 20 that implements visualization of catheter-tissue contact by map distortion, in accordance with an embodiment of the present invention. System 20 comprises a probe 22, such as a catheter, and a control console 24. In the embodiment described hereinbelow, it is assumed that probe 22 is used for diagnostic or therapeutic treatment, such as for mapping electrical potentials in a heart 26 of a patient 28. Alternatively, probe 22 may be used, mutatis mutandis, for other therapeutic and/or diagnostic purposes in the heart or in other body organs.

An operator 30 inserts probe 22 through the vascular system of patient 28 so that a distal end 32 of probe 22 enters a chamber of heart 26. System 20 typically uses magnetic position sensing to determine position coordinates of distal end 32 inside heart 26. Console 24 comprises a driver circuit 34, which drives field generators 36 placed at known positions external to patient 28, e.g., below the patient's torso. A magnetic field sensor 38 within distal end 32 of probe 22 (sensor 38 is shown in more detail in FIG. 2) generates electrical signals in response to the magnetic fields from the coils, thereby enabling console 24 to determine the position of distal end 32 within the chamber.

Although in the present example system 20 measures the position of distal end 32 using magnetic-based sensors, other position tracking techniques may be used (e.g., impedance-based sensors). Magnetic position tracking techniques are described, for example, in U.S. Pat. Nos. 5,391,199, 5,443, 489, 6,788,967, 6,690,963, 5,558,091, 6,172,499 6,177,792, whose disclosures are incorporated herein by reference. Impedance-based position tracking techniques are described, for example, in U.S. Pat. Nos. 5,983,126, 6,456,864 and 5,944,022, whose disclosures are incorporated herein by reference.

In order to map the cardiac chamber in question, operator 30 positions distal end 32 at multiple positions on (or in close proximity to) the inner surface of the chamber. At each position, an electrode 40 coupled to the distal end measures a certain physiological property (e.g., the local surface electrical potential). System 20 correlates the position measurements and the electrical potential measurements. Thus, the system collects multiple map points, with each map point comprising a coordinate on the inner chamber surface and a respective physiological property measurement at this coordinate.

Console 24 comprises a processor 42, which collects image data from a medical imaging system (not shown) such as a magnetic resonance imaging (MRI) system, or a computed tomography (CT) system, or a probe mapping system such as the CARTO™ mapping system produced by Biosense Webster Inc., of Diamond Bar, Calif. Processor 42 uses the image data to construct a simulated surface of the cardiac chamber in question. An example method for constructing the simulated surface is described further below. Processor 42 then "lays" the electrical potential measurements over the simulated surface produced from the image data. Processor 42 displays an image 44 of the simulated surface, with the electrical potential measurements laid thereon (the fusion of the simulated surface and the potential measurements is referred to herein as a map), to operator 30 on a display 46.

Processor 42 typically comprises a general-purpose computer, with suitable front end and interface circuits for receiving signals from probe 22 and controlling the other components of console 24. Processor 42 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 42 may be carried out by dedicated or programmable digital hardware components.

In the present embodiment, processor 42 also monitors the signal measurements received from a force sensor 48 within distal end 32 (force sensor 48 is shown in more detail in FIG. 2), in order to make an accurate evaluation of the force exerted by distal end 32 on endocardial tissue of heart 26. When the force exerted by distal end 32 on the endocardial tissue exceeds a predefined amount, processor 42 may create a distorted surface in image 44 indicating the exerted force.

Processor 42 stores data representing image 44 in a memory 50. In some embodiments, operator 30 using one or more input devices 52, can control how processor 42 presents the distortion. For example, if image 44 comprises a three-dimensional representation of heart 26, the operator can use input devices 52 to control the actual geometrical extent of a vertex representing the force exerted by the distal end. (Such a vertex may occur in a generally conical form if tissue tenting occurs.) Additionally or alternatively, operator 30 can use input devices 52 to control any coloring and/or shading used to indicate the exerted force.

Although FIG. 1 shows a particular system configuration, other system configurations can also be employed to implement embodiments of the present invention, and are thus considered to be within the spirit and scope of the present invention. For example, the methods described hereinbelow may be applied using position transducers of types other than the magnetic field sensor described above, such as impedance-based or ultrasonic position sensors. The term "position transducer" as used herein refers to an element mounted on probe 22 which causes console 24 to receive signals indicative of the coordinates of the distal end. The position transducer may thus comprise a receiver on the probe, which generates a position signal to the control unit based on energy received by the transducer; or it may comprise a transmitter, emitting energy that is sensed by a receiver external to the probe. Furthermore, the methods described hereinbelow may similarly be applied in therapeutic and diagnostic applications using not only catheters, but also probes of other types, both in the heart and in other body organs and regions.

Figure 2:
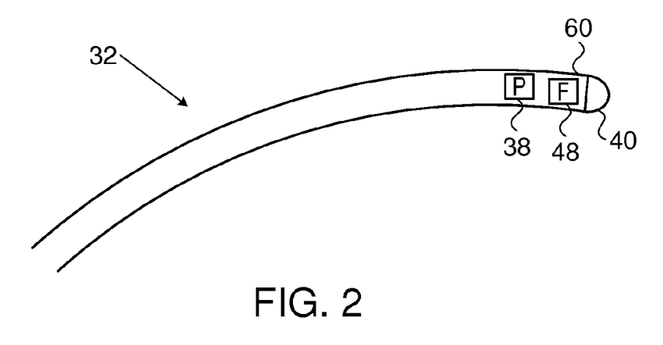
FIG. 2 is a schematic side view showing details of the distal portion of the force-sensing catheter, in accordance with an embodiment of the present invention.

FIG. 2 is a schematic sectional view of distal end 32 of probe 22, in accordance with an embodiment of the present invention. Specifically, FIG. 2 shows functional elements of distal end 32 used for therapeutic and/or diagnostic activity. Electrode 40 at a distal tip 60 of the probe senses electrical signals in the tissue. Electrode 40 is typically made of a metallic material, such as a platinum/iridium alloy or another suitable material. Alternatively, multiple electrodes (not shown) along the length of the probe may be provided.

Position sensor 38 transmits a signal to console 24 that is indicative of the location coordinates of distal end 32. Position sensor 38 may comprise one or more miniature coils, and typically comprises multiple coils oriented along different axes. Alternatively, position sensor 38 may comprise either another type of magnetic sensor, an electrode that serves as a position transducer, or position transducers of other types, such as impedance-based or ultrasonic position sensors. Although FIG. 2 shows a probe with a single position sensor, embodiments of the present invention may utilize probes with more than one position sensor.

In an alternative embodiment, the roles of position sensor 38 and magnetic field generators 36 may be reversed. In other words, driver circuit 34 may drive a magnetic field generator in distal end 32 to generate one or more magnetic fields. The coils in generator 36 may be configured to sense the fields and generate signals indicative of the amplitudes of the components of these magnetic fields. Processor 42 receives and processes these signals in order to determine the position coordinates of distal end 32 within heart 26.

Force sensor 48 measures a force applied by distal tip 60 to the endocardial tissue of heart 26 by generating a signal to the console that is indicative of the force exerted by the distal tip on the endocardial tissue. In one embodiment, the force sensor may comprise a magnetic field transmitter and receiver connected by a spring in distal end 32, and may generate an indication of the force based on measuring the deflection of the spring. Further details of this sort of probe and force sensor are described in U.S. Patent Application Publications 2009/0093806 and 2009/0138007, whose disclosures are incorporated herein by reference. Alternatively, distal end 32 may comprise another type of force sensor.

Figure 3:
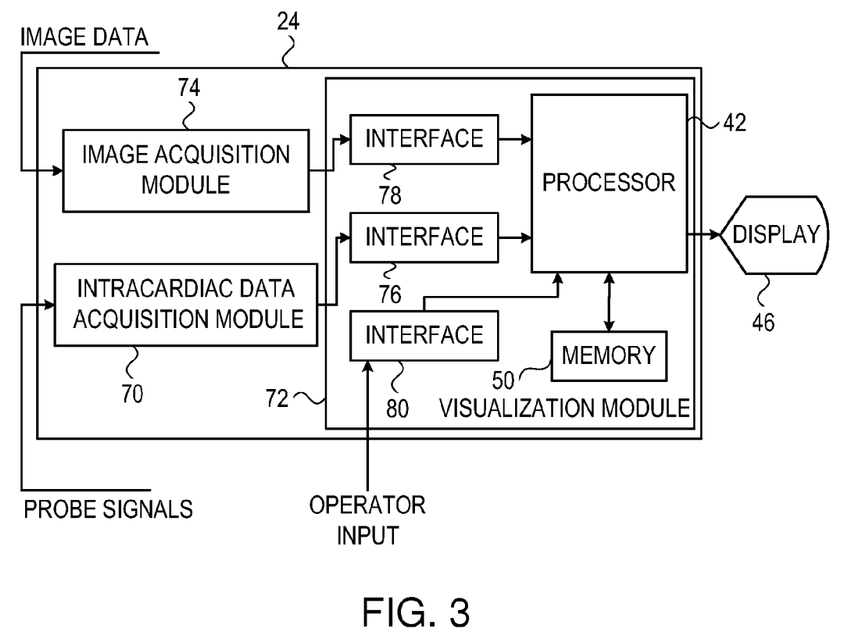
FIG. 3 is a block diagram that schematically illustrates elements of the catheter-tissue contact visualization system, in accordance with a disclosed embodiment of the present invention.

FIG. 3 is a block diagram that schematically illustrates elements of console 24, in accordance with a disclosed embodiment of the present invention. An intracardiac data acquisition module 70 collects force measurements and position signals from probe 22, and conveys the measurements and signals to a visualization module 72. An image acquisition module 74 collects image data for heart 26 (typically from an MRI or CT system, as described supra), and conveys the image data to module 72. Module 72 comprises interfaces 76 and 78 for communicating with modules 70 and 74, respectively.

Processor 42 typically stores the collected image data to memory 50. Memory 50 may comprise any suitable volatile and/or non-volatile memory, such as random access memory or a hard disk drive. After collecting the image data, processor 42 applies an algorithm (e.g., a fast mapping process) to construct image 44. In the present embodiment, image 44 comprises a simulated 3D surface (e.g., a polygon mesh) of a surface of the cardiac chamber, which processor 42 presents as image 44 on display 46.

If the collected force measurements exceed a predefined amount, processor 42 may distort image 44 in order to provide operator 30 with a visual representation of the force between distal end 32 and the endocardial tissue. As discussed supra, examples of the distortion include, but are not limited to a vertex in the simulated surface, as well as coloring and/or shading of a region in the simulated surface corresponding to a location in heart 26 where distal end 32 is applying the force.

Inputs from input devices 52 via an interface 58 enable operator 30 to adjust the visualization of the distortion. For example, operator 30 can determine how processor 42 presents the distortion on display 46. In other words, based on the operator input, the distortion shown on the simulated surface may not necessary reflect the actual distortion of the heart (e.g., the distortion may exaggerate the force).

Catheter-Tissue Contact Visualization

Figure 4:
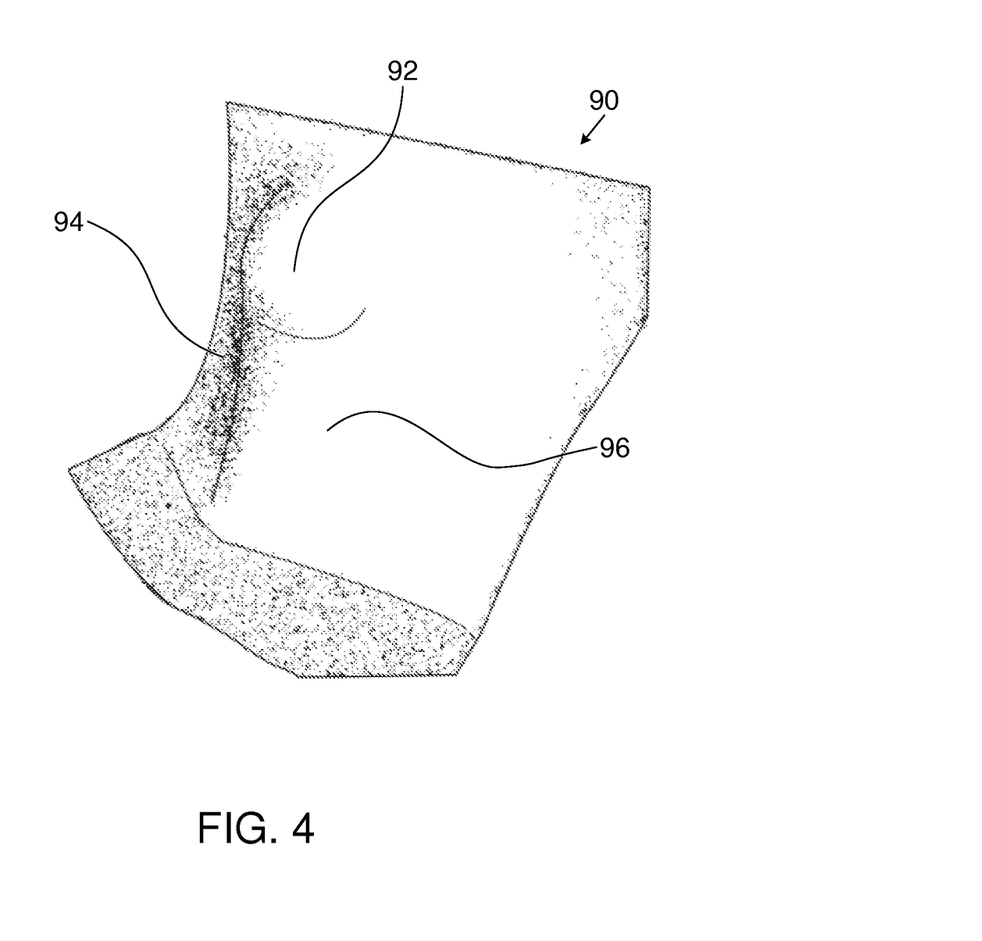
FIG. 4 is an illustration of a distortion indicating catheter-tissue contact, in accordance with an embodiment of the present invention.

FIG. 4 is an illustration of a simulated surface 90 showing distortion indicating catheter-tissue contact, in accordance with an embodiment of the present invention. In the example shown, simulated surface 90 represents a portion of a wall of heart 26 viewed from the outside of the heart. In the example shown, distal end 32 is pressing against endocardial tissue in heart 26, i.e., catheter 22 is within heart 26 and pressing against the heart wall. The distortion displayed in simulated surface 90 due to the force exerted by distal end 32 on the heart wall is displayed in a gray scale format as a protruding vertex 92, a dark portion 94, and a light portion 96, thus incorporating a 3D shadowed effect on the surface. Alternatively, simulated surface 90 may be visualized from inside heart 26, in which case the distortion may be displayed as a recessed vertex (i.e., a depression in surface 90 instead of protrusion 92). Further alternatively, the distortion may be displayed in a color format.

Figure 5:
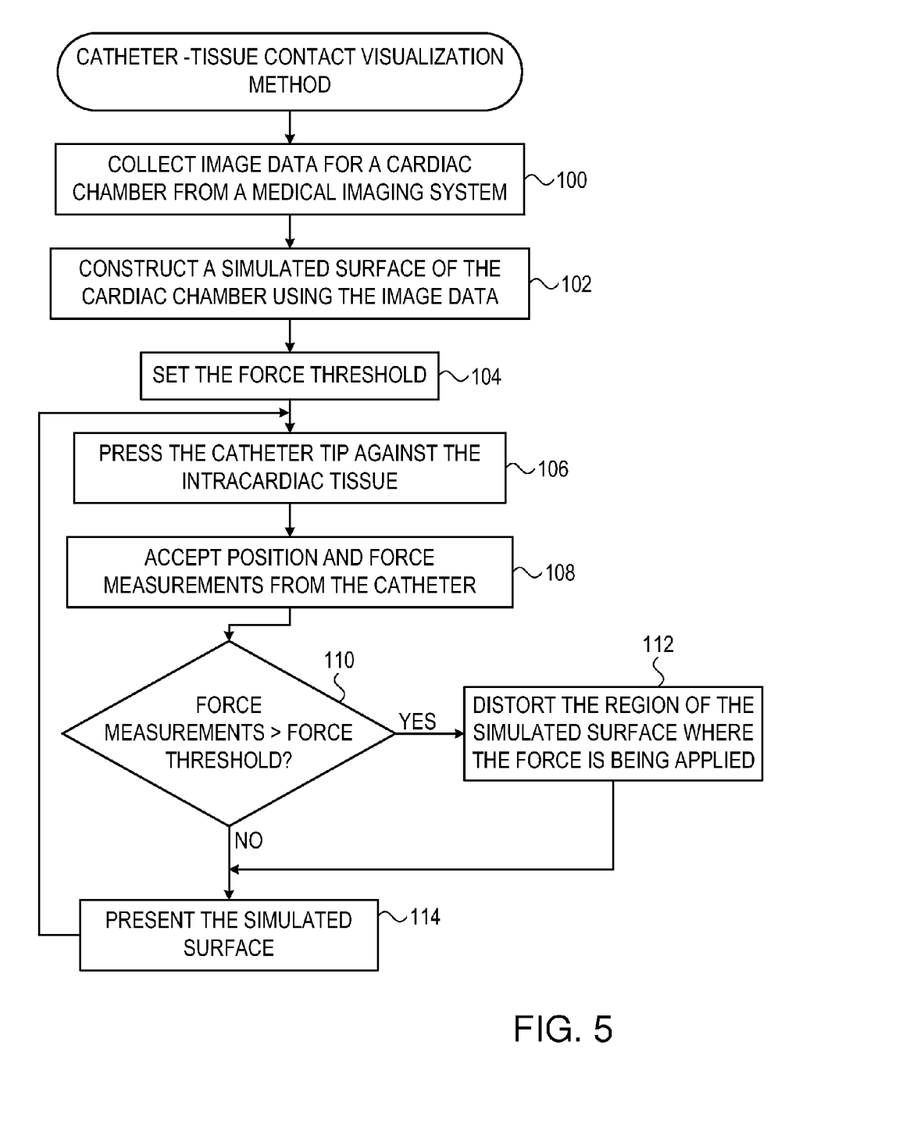
FIG. 5 is a flow diagram that schematically illustrates a method of visualizing catheter-tissue contact, in accordance with an embodiment of the present invention.

FIG. 5 is a flow diagram that schematically illustrates a method of creating a distortion in map 44 in order to visualize catheter-tissue contact, in accordance with an embodiment of the present invention. Prior to performing an intracardiac procedure, processor 42 collects image data for a chamber of heart 26 from a medical imaging system (e.g., a CARTO™ or an MRI or a CT imaging system), in a first collection step 100.

The image data typically comprises data points representing tissue of the chamber. In a construction step 102, processor 42 applies an algorithm (e.g., a fast mapping process) to the collected image data in order to construct simulated surface 90.

In a threshold set step 104, using input devices 52, operator 30 sets a predefined amount which defines a force threshold. Alternatively, the predefined amount may be defined in advance, and stored in memory 50.

During the intracardiac procedure, in a positioning step 106, operator 30 positions probe 22 so that distal end 32 of the probe is pressing against endocardial tissue of heart 26. In a second collection step 108, processor 42 accepts signals from position sensor 38 indicating a position measurement for distal end 32 within heart 26, and signals from force sensor 48 indicating a measurement of the force between distal end 32 and the endocardial tissue.

In a comparison step 110, if the force measurement exceeds the force threshold, then in a distortion step 112, processor 42 creates a distortion (e.g., protrusion 92) on simulated surface at the location indicated by the position measurement, thereby forming a distorted surface. Operator 30 can control the magnitude of the distortion and/or the distortion type (e.g., a protrusion or coloring/shading) using input devices 52. Additionally, processor 42 may adjust the magnitude of the distortion depending on the tissue in contact with distal end 32. For example, since an atrium of heart 26 has a thinner wall than a ventricle (of the heart), processor 42 may introduce a greater degree of distortion in map 44 when the distal end is in contact with atrial tissue (and applying an equivalent force).

In a display step 114, processor 42 presents map 44 which comprises the simulated surface (including any distortion) and relevant potential measurements on display 46, and the method returns to step 106 until operator 30 completes the intracardiac procedure. Returning to step 110, if the measured force is less than the force threshold, then the method continues with step 114, without introducing any distortion to simulated surface 90.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
constructing a surface of a body cavity from image data obtained from a medical imaging system;
pressing a distal end of a probe against a wall of the body cavity;
while pressing the distal end against the wall, accepting, from the probe, position measurements indicating a position of the probe within the body cavity, physiological property measurements indicating a physiological property of the body cavity and force measurements indicating a force between the distal end and the wall;
generating an anatomical map of the body cavity using the position measurements and the physiological property measurements;
combining the surface and the anatomical map by laying the anatomical map over the surface;
distorting the shape of the surface at the position indicated by the position measurements by incorporating a three dimensional effect on the surface, so as to form a distorted surface, upon detecting that the force measurements exceed a predefined amount; and
displaying the combined distorted surface and the anatomical map, the three dimensional effect being a visual indicator of the amount of force caused by the pressing.

2. The method according to claim 1, wherein the medical imaging system is selected from a group consisting of a probe mapping system, a magnetic resonance imaging system and a computed tomography system.

3. The method according to claim 1, wherein constructing the surface comprises applying a mapping process to the image data.

4. The method according to claim 1, wherein the probe comprises an intracardiac catheter.

5. The method according to claim 1, wherein the body cavity comprises a chamber of a heart.

6. The method according to claim 1, wherein the three dimensional effect comprises a vertex protruding from the surface.

7. The method according to claim 1, wherein the three dimensional effect comprises a vertex recessing into the surface.

8. The method according to claim 1, further including filling a region of the three-dimensional effect on the surface with a specific color corresponding to the force at the position indicated by the position measurements.

9. An apparatus, comprising:
a probe configured for insertion into a body cavity of a patient, the probe having a position sensor for measuring a position of a distal end of the probe inside the body cavity, a sensor measuring a physiological property of the body cavity and a force sensor for measuring a force between the distal end and a wall of the body cavity; and
a processor configured to:
construct a surface of the body cavity, to accept from the probe, while pressing the distal end against the wall, position measurements indicating a position of the probe within the body cavity, physiological property measurements indicating a physiological property of the body cavity and force measurements indicating a force between the distal end and the wall,
generate an anatomical map of the body cavity using the position measurements and the physiological property measurements;
combine the surface and the anatomical map by laying the anatomical map over the surface;

distort the shape of the surface at the position indicated by the position measurements by incorporating a three-dimensional effect on the surface, so as to form a distorted surface, upon detecting that the force measurements exceed a predefined amount, and display the combined distorted surface and anatomical map, the three dimensional effect being a visual indicator of the amount of force caused by the pressing.

10. The apparatus according to claim 9, wherein the medical imaging system is selected from a group consisting of a probe mapping system, a magnetic resonance imaging system and a computed tomography system.

11. The apparatus according to claim 9, wherein the processor is configured to construct the surface by applying a mapping process to the image data.

12. The apparatus according to claim 9, wherein the probe comprises an intracardiac catheter.

13. The apparatus according to claim 12, wherein the three dimensional effect comprises a vertex protruding from the surface.

14. The apparatus according to claim 12, wherein the three dimensional effect comprises a vertex recessing into the surface.

15. The apparatus according to claim 9, wherein the processor is configured to fill a region of the three-dimensional effect on the surface with a specific color corresponding to the force at the position indicated by the position measurements.

16. A computer software product, operated in conjunction with a probe that is configured for insertion into a body cavity of a patient and includes a position sensor for measuring a position of a distal end of the probe inside the body cavity, a sensor measuring a physiological property of the body cavity and a force sensor for measuring a force between the distal end and a wall of the body cavity, the product comprising a non-transitory computer-readable medium, in which program instructions are stored, which instructions, when read by a computer, cause the computer to:

construct a surface of the body cavity, to accept from the probe, while pressing the distal end against the wall, position measurements indicating a position of the probe within the body cavity, physiological property measurements indicating a physiological property of the body cavity and force measurements indicating a force between the distal end and the wall, generate an anatomical map of the body cavity using the position measurements and the physiological property measurements;

combine the surface and the anatomical map by laying the anatomical map over the surface;

distort the shape of the surface at the position indicated by the position measurements by incorporating a three-dimensional effect on the surface, so as to form a distorted surface, upon detecting that the force measurements exceed a predefined amount, and to display the combined distorted surface and anatomical map, the three dimensional effect being a visual indicator of the amount of force caused by the pressing.

17. The computer software product according to claim 16, wherein the instructions cause the computer to:

fill a region of the three-dimensional effect on the surface with a specific color corresponding to the force at the position indicated by the position measurements.

* * * * *